United States Patent
Senn

(10) Patent No.: US 7,282,212 B2
(45) Date of Patent: Oct. 16, 2007

(54) CONTROL OF WOOD-DESTROYING PESTS WITH THIAMETHOXAM

(75) Inventor: Robert Senn, Basel (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/363,500

(22) PCT Filed: Aug. 27, 2001

(86) PCT No.: PCT/EP01/09859

§ 371 (c)(1),
(2), (4) Date: Feb. 25, 2003

(87) PCT Pub. No.: WO02/17720

PCT Pub. Date: Mar. 7, 2002

(65) Prior Publication Data

US 2003/0181448 A1  Sep. 25, 2003

(30) Foreign Application Priority Data

Aug. 28, 2000 (CH) ..................... 1672/00

(51) Int. Cl.
*A01N 25/28* (2006.01)
(52) U.S. Cl. ............ 424/417; 424/405; 424/408; 424/84; 514/229.2; 514/407; 514/531; 514/365
(58) Field of Classification Search ............ 424/405, 424/408–411, 84, DIG. 11; 574/365
See application file for complete search history.

(56) References Cited

U.S. PATENT DOCUMENTS

| | | | |
|---|---|---|---|
| 6,255,340 B1 * | 7/2001 | Fujimoto | 574/471 |
| 6,284,782 B1 * | 9/2001 | Fujimoto | 514/372 |
| 6,479,543 B1 * | 11/2002 | Treacy et al. | 514/522 |
| 6,503,904 B2 | 1/2003 | Schneidersmann | |
| 6,875,727 B2 * | 4/2005 | Hofer et al. | 504/100 |
| 2001/0023552 A1 | 9/2001 | Fujimoto | |
| 2002/0177597 A1 * | 11/2002 | Treacy et al. | 514/229.2 |

FOREIGN PATENT DOCUMENTS

| | | |
|---|---|---|
| JP | 11-292723 | * 10/1999 |
| JP | 11292723 | 10/1999 |
| WO | 0028825 | 5/2000 |

OTHER PUBLICATIONS

Patent Abstracts of Japan, vol. 2000, No. 1; Jan. 2000.

* cited by examiner

*Primary Examiner*—Neil S. Levy
(74) *Attorney, Agent, or Firm*—William A. Teoli, Jr.

(57) ABSTRACT

There are described a method for the control of wood pests which comprises applying to the pests or to their habitat a pesticidally active amount of a pesticidal composition comprising, as active ingredient, at least a compound of formula

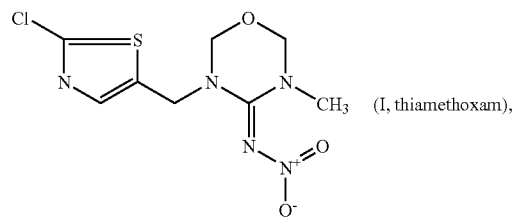

(I, thiamethoxam), in free form or in the form of an agrochemically acceptable salt, and at least one adjuvant; the corresponding use of those compounds, pesticidal compositions whose active ingredient is selected from those compounds, a process for the preparation of such compositions, the use of such compositions, and plant propagation material accordingly protected against pest attack.

6 Claims, No Drawings

CONTROL OF WOOD-DESTROYING PESTS WITH THIAMETHOXAM

This application is a 371 filing of International Application No. PCT/EP01/09859, filed Aug. 27, 2001, the contents of which are incorporated herein by reference.

The invention relates to a method of controlling wood pests which comprises applying to the pests or to their habitat a pesticidally active amount of a pesticidal composition comprising, as active ingredient, at least a compound of formula

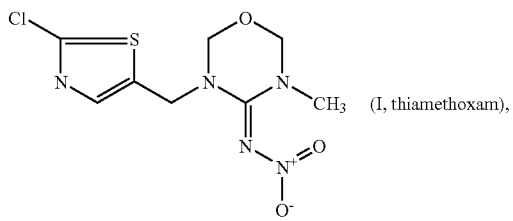

(I, thiamethoxam), in free form or in the form of an agrochemically acceptable salt, and at least one adjuvant; to the corresponding use of those compounds, to pesticidal compositions comprising thiamethoxam as active ingredient, to a process for the preparation of such compositions, to the use of such compositions, and also to plant propagation material accordingly protected against pest attack.

The compound used according to the invention, thiamethoxam (3-(2-chloro-1,3-thiazol-5-ylmethyl)-5-methyl-1,3,5-oxadiazinan-4-ylidene(nitro)amine), is known to the person skilled in the art, for example from The Pesticide Manual, The British Crop Protection Council, Twelfth Edition, page 896.

Agrochemically acceptable salts of thiamethoxam are, for example, acid addition salts. Those acid addition salts are formed, for example, with strong inorganic acids, such as mineral acids, e.g. perchloric acid, sulfuric acid, nitric acid, nitrous acid, a phosphoric acid or a hydrohalic acid, with strong organic carboxylic acids, such as unsubstituted or substituted, e.g. halo-substituted, $C_1$-$C_4$alkanecarboxylic acids, e.g. formic acid, acetic acid or trifluoro-acetic acid, saturated or unsaturated dicarboxylic acids, e.g. oxalic, malonic, succinic, maleic, fumaric and phthalic acid, hydroxycarboxylic acids, e.g. ascorbic, lactic, malic, tartaric and citric acid, or benzoic acid, or with organic sulfonic acids, such as unsubstituted or substituted, e.g. halo-substituted, $C_1$-$C_4$alkane- or aryl-sulfonic acids, e.g. methane- or p-toluene-sulfonic acid. The compound used according to the invention in free form and in the form of its agrochemically acceptable salts is to be understood hereinbefore and hereinafter as including, where appropriate, the corresponding salts and the free compound, respectively. Preference is given to thiamethoxam in free form.

Many different classes of active ingredient are mentioned in the literature as arthropodicidally active ingredients for controlling termites. It has now been found, surprisingly, that the compound thiamethoxam has especially advantageous activity against wood pests, especially against termites, more especially representatives of the order Isoptera.

Termites include especially the families Hodotermitidae, Kalotermitidae (Incisitermes), Rhinotermitidae and Termitidae. The method according to the invention controls, especially, termites of the genera and species: *Allondothermes* spp., for example *A. giffardi* and *A. tenax;* Ancistrotermes, for example *A. cavithorax, A. guineensis, A. latinotus* and *A. periphrasis;* Amitermes spp., for example *A. evuncifer;* Cryptotermes spp., for example *C. brevis* and *C. cavifrons;* Heterotermes spp., for example *H. aureus, H. indicola* and *H. tenuis;* Hodotermes spp., for example *H. mossambicus;* Macrotermes spp., for example *M. michaelseni, M. falcifager, M. bellicosus, M. subhyalinus* and *M. natalensis;* Microtermes spp., for example *M. albopartitus, M. redenianus, M. lepidus, M. traghardi* and *M. thoracalis;* Nasutitermes spp., for example *N. costalis;* Neotermes spp., for example *N. gestroi* and *N. jouteli;* Odontotermes spp., for example *O. bruneus, O. classicus, O. smeathmani, O. lathericius* and *O. badius;* Paraneothermes spp., for example *P. simplicicornis;* Pseudacanthotermes spp., for example *P. militaris* and *P. spiniger;* Reticulitermes spp., for example *R. flavipes, R. virginicus, R. tibialis, R. humilis, R. santonensis* and *R. hesperus;* Coptotermes spp., for example *C. formosanus* and *C. crassus;* Zootermopsis spp., for example *Z. angusticollis* and *Z nevadensis;* Incisitermes (Kalotermes) spp., for example *I. minor;* Marginitermes spp., for example *M. hubbardi;* Prorhinotermes spp., for example *P. simplex;* Termes spp., for example *T. fatalis;* Trinervitermes spp., for example *T. trinervius;* very especially *Odontotermes smeathmani, Trinervitermes trinervius* and *Amitermes evuncifer.*

Preferred is a method according to the instant invention for controlling subterranean termites, especially of *Reticulitermes, Coptotermes* and *Zootermopsis;* very especially *Reticulitermes.* Also preferred is a method according to the instant invention for controlling drywood termites, especially *Cryptotermes, Incisitermes* and *Neotermes.* Another preferred embodiment of the instant invention is a method for controlling powderpost (furniture) termites, especially *Cryptotermes.*

On the one hand, preferred is the control of structural termites which damage buildings. On the other hand, also the control of agricultural species is preferred. Agricultural termite species are those termites which damage crops.

Further pests that cause damage to wood by feeding on wood, living on wood or reproducing on wood are understood to include, for example, wood-boring insects such as representatives of the family Lyctidae, of the family Apidae, for example *Xylocopa virginica,* and of the family Anobiidae, e.g. *Anobium punctatum.*

Termites can cause considerable damage to buildings, crops and stored goods especially in geographical latitudes between 42° N and 42° S. Two kinds of termites are in principle differentiated:

Subterranean termites which are the most widespread, require warm air and a moist environment. In order that such termites always have access to the necessary moisture, they must have a direct connection to moist soil. Damage by termites that are active underground is almost always associated with damage to wood.

Termites whose habitat is on dry wood, although less common, represent a major problem because they do not require contact with moist ground. They gain access to buildings under roof shingles and through cracks and air vents. Others are also brought into homes by way of furniture that is already infested. Pretreating wood is considered the most effective method of controlling such termites. Because the damage caused by termites living on dry wood is produced more slowly than that caused by termites living in a moist environment, damage by the former is found especially in old buildings.

Damage by termites living underground in a moist environment can be prevented especially by applying insecticidally active substances to the termites or to their habitat. Such compounds are conventionally used especially by application to the ground around the buildings, crops and stored goods.

The currently available compositions for controlling termites are not satisfactory in all respects because comparatively large areas around building structures, or the buildings themselves, usually have to be treated with large amounts of insecticide. That can lead to subsequent problems especially in houses, more especially when persistent pesticides are used. There therefore exists a further need for improved solutions, especially using an active ingredient that can be used in especially small amounts and that is of low volatility.

The invention accordingly relates also to pesticidal compositions comprising thiamethoxam, such as emulsifiable concentrates, suspension concentrates, directly sprayable or dilutable solutions, coatable pastes, dilute emulsions, wettable powders, soluble powders, dispersible powders, wettable powders, dusts, granules, pellets, aerosols or encapsulations in polymer substances, the type of formulation being chosen in accordance with the intended objectives and prevailing circumstances. Such compositions used against wood pests are, for example, of the same kind as those described in EP-A-736 252.

Thiamethoxam is used in those compositions in pure form, for example in a specific particle size, or preferably together with—at least—one of the adjuvants or carriers customary in formulation technology.

Formulation adjuvants used are, for example, solid carriers, solvents, stabilisers, "slow release" adjuvants, colorants and optionally surface-active substances (surfactants). Suitable carriers and adjuvants include any substances customarily used in plant protection compositions. Suitable adjuvants, such as solvents, solid carriers, surface-active compounds, non-ionic surfactants, cationic surfactants, anionic surfactants and other adjuvants in the compositions used according to the invention include, for example, the same substances as those described in EP-A-736 252, page 7, line 51 to page 8, line 39, which are included in the present application by reference.

The compositions to be used according to the invention for controlling wood pests are prepared in known manner, in the absence of adjuvants, for example by grinding and/or sieving, for example to a specific particle size, or compressing the active ingredient, or in the presence of at least one adjuvant, for example by intimately mixing and/or grinding the active ingredient with the adjuvant(s). The invention relates also to those processes for the preparation of the compositions according to the invention and to the use of thiamethoxam in the preparation of those compositions.

The compositions usually comprise 0.1 to 99%, especially 0.1 to 95%, of active ingredient, and 1 to 99.9%, especially 5 to 99.9%, of—at least—one solid or liquid adjuvant, it generally being possible for 0 to 25%, especially 0.1 to 20%, of the compositions to be surfactants (in each case percentages are by weight). Whereas commercial products will preferably be formulated as concentrates, the end user will also often employ dilute formulations which have substantially lower active ingredient concentrations. Preferred formulations have especially the following composition (%=percent by weight):

| Emulsifiable concentrates: | |
| --- | --- |
| thiamethoxam: | 1 to 90%, preferably 5 to 20% |
| surfactant: | 1 to 30%, preferably 10 to 20% |
| solvent: | 5 to 98%, preferably 70 to 85% |
| Dusts: | |
| thiamethoxam: | 0.1 to 10%, preferably 0.1 to 1% |
| solid carrier: | 99.9 to 90%, preferably 99.9 to 99% |
| Suspension concentrates: | |
| thiamethoxam: | 5 to 75%, preferably 10 to 50% |
| water: | 94 to 24%, preferably 88 to 30% |
| surfactant: | 1 to 40%, preferably 2 to 30% |
| Wettable powders: | |
| thiamethoxam: | 0.5 to 90%, preferably 1 to 80% |
| surfactant: | 0.5 to 20%, preferably 1 to 15% |
| solid carrier: | 5 to 99%, preferably 15 to 98% |
| Granules: | |
| thiamethoxam: | 0.5 to 30%, preferably 3 to 15% |
| solid carrier: | 99.5 to 70%, preferably 97 to 85% |

The activity of the compositions according to the invention can be substantially broadened and adapted to prevailing circumstances by the addition of other, for example insecticidal, acaricidal and/or fungicidal, active ingredients. Examples of suitable additional insecticidal and acaricidal active ingredients include representatives of the following classes of compounds: organophosphorus compounds, nitrophenols and derivatives, formamidines, nitroenamine derivatives, nitro- and cyano-guanidine derivatives, ureas, benzoylureas, carbamates, pyrethroids, chlorinated hydrocarbons and *Bacillus thuringiensis* preparations. Especially preferred mixing partners are, for example, azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; jodfenphos; kinoprene; lufenuron; methacriphos; methidathion; monocrotophos; phosphamidon; profenofos; diofenolan; a substance obtainable from the *Bacillus thuringiensis* strain GC91 or from NCTC11821; pymetrozine; bromopropylate; methoprene; disulfoton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; avermectin $B_1$ (abamectin); emamectin; spinosad; a plant extract that is active against insects; a preparation comprising nematodes that are active against insects; a preparation obtainable from *Bacillus subtilis;* a preparation comprising fungi that are active against insects; a preparation comprising viruses that are active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxim; butylpyridaben; cadusafos; carbaryl; carbophenothion; chloethocarb; chlorethoxyfos; chlormephos; cisresmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethofenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; iprobenfos; isofenphos; isoxathion; ivermectin; malathion; mecarbam; mesulfenphos; metaldehyde; metolcarb; milbemectin; moxidectin; naled; NC 184; omethoate; oxamyl; oxydemeton M; oxydeprofos; permethrin; phenthoate; phorate; phosmet; phoxim; pirimiphos M; pirimiphos E; promecarb; propaphos; prothiofos; prothoate; pyrachlophos; pyridaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiodicarb; thiofanox; thionazin; thuringiensin; tralomethrin; triarthene; triazophos; triazuron; trichlorfon; triflumuron; trimethacarb; vamidothion; xylylcarb; YI 5301/5302; zetamethrin; DPX-MP062-indoxacarb; methoxyfenozide; bifenazate; XMC (3,5-xylyl methylcarbamate) or the fungal pathogen *Metarhizium anisopliae;* very especially fipronil, abamectin, emamectin, spinosad and lambda-cyhalothrin.

Another embodiment is a method for protecting wood from the attack of wood-destroying pests.

In an especially preferred embodiment of the invention, a composition comprising thiamethoxam is used to control termites and/or other wood-destroying pests in the ground, by means of which indirect protection of wood structures, crops and stored goods is achieved.

For that purpose, an amount of thiamethoxam sufficient for controlling the pests is applied to the ground, preferably at a rate of application of from 1 g to 2000 g, especially from 5 to 1000 g, more especially from 10 to 500 g, per hectare.

Worker termites have to walk on the ground that has been treated with the pesticide in order to reach the wood, inevitably taking up some of the pesticide in the process and carrying it back into the termite nest, and consequently spreading the active ingredient in the termite nest.

The active ingredient can therefore also be presented in the form of bait, for example in the form of tablets comprising the active ingredient, e.g. as described in U.S. Pat. No. 5,096,710. Special preference is given to application of the composition to materials that are used by the termites as food and as building materials for the termite nest. Examples of such materials are cardboard, paper, wood, wood dust, cellulose powder or cotton. Suitable concentrations on such materials are from 0.01 to 10 000 ppm. Such bait is especially effective when pheromones are also employed and wood is used that is already infested with fungi. Such modes of application are discussed, for example, in U.S. Pat. No. 5,151,443.

Another especially preferred method of controlling termites is the application of the active ingredient in the form of microcapsules. A further preferred method is the incorporation of the active ingredient into the building materials, e.g. insulating foam and fireboard. Another preferred method is the application of the active ingredient via slow release polymer matrices.

In the area of wood pest control, the compositions according to the invention are valuable preventive and/or curative compositions having a very advantageous biocidal spectrum even at low rates of concentration, while being well tolerated by warm-blooded animals, fish and plants. The compound or compound mixtures of the invention are effective against all or individual development stages of normally sensitive wood pests, but also of resistant wood pests, especially termites. The action of thiamethoxam may manifest itself directly, i.e. in the mortality of the pests, which occurs immediately or only after some time, or indirectly, for example in reduced oviposition and/or hatching rate, good activity corresponding to a mortality of at least 50 to 60%.

With the compositions according to the invention it is also possible to avoid or reduce damage caused to plants by wood pests, especially to control pests of the said kind on useful plants and ornamentals in agriculture, in horticulture and in forestry, or on parts of such plants, such as the fruit, bölossom, leaves, stems, tubers or roots, while in some cases parts of the plants that grow later are also still protected against those pests. Suitable target crops in the context of controlling the said wood pests include especially cereals, such as wheat, barley, rye, oats, rice, maize, sorghum, millet and manioc; beet, such as sugar beet and fodder beet; fruit, such as pomes, stone fruit and soft fruit, such as apples, pears, plums, peaches, almonds, cherries, or berries, for example strawberries, raspberries and blackberries; leguminous plants, such as beans, lentils, peas and soybeans; oil plants, such as rape, mustard, poppy, olives, sunflowers, coconut, castor oil plants, cocoa beans and groundnuts; cucurbitaceae, such as marrows, cucumbers and melons; fibre plants, such as cotton, flax, hemp and jute; citrus fruit, such as oranges, lemons, grapefruit and mandarins; vegetables, such as spinach, lettuce, asparagus, cabbages, carrots, onions, tomatoes, potatoes and paprika; lauraceae, such as avocados, cinnamon and camphor; and tobacco, nuts, coffee, aubergines, sugar cane, tea, pepper, vines, hops, bananas, natural rubber plants, eucalyptus, as well as ornamentals. Especially preferred areas of use are crops of groundnuts, cocoa beans, sugar cane, coconut, rice, cotton, millet, maize, manioc, sorghum and eucalyptus.

Further areas of use according to the invention include the protection of stored goods and storerooms and raw materials from wood pests.

The Examples that follow serve to illustrate the invention. They do not limit the invention.

APPLICATION EXAMPLES

Example A1

Activity Against Termites

Wood bait is treated with different amounts of thiamethoxam and the influence on the hatching rate and survival of termites is tested. Solutions having concentrations of 0 ppm, 0.1 ppm, 100 ppm and 1000 ppm of thiamethoxam in acetone are used. Water is used in the control study. The bait consists of pine wood that has been kept for four months in a natural environment.

The termites are collected in the environment from infested pieces of wood. For the wood bait study, the wood is held in an oven at 80° C. for 48 hours. The dried wood is then weighed and the pieces are placed in solutions of thiamethoxam of the desired concentration for 18 hours. The pieces of wood are then removed from the solutions, dried in air and re-weighed. In order to determine the activity of the bait against termites, the pieces of wood so treated are placed on a thin layer of untreated soil in petri dishes.

The termites (50 workers and 2 soldiers) are introduced into each petri dish. The dishes are inspected three times a week for 8 weeks. The development of the insects, abnormalities and mortality are recorded. After 8 weeks, the blocks of wood are rinsed with water and again dried in an oven at 80° C. for 48 hours. The weight of each piece of wood is then re-determined. The difference in the weights gives the amount of wood consumed by the termites.

The compositions according to the invention exhibit good activity in this test.

What is claimed is:

1. A method of controlling termites, which comprises applying to the termites or to their habitat a termiticidally effective amount of a termiticidal composition comprising:
   (a) a termiticidal active ingredient (i) consisting of thiamethoxam, in free form or in the form of an agrochemically acceptable salt, or (ii) consisting of thiamethoxam, in free form or in agrochemically acceptable salt form and at least one insecticide mixing partner selected from fipronil and lambda-cyhalothrin; and
   (b) at least one adjuvant.

2. The method according to claim 1, characterised in that thiamethoxam in free form is used.

3. The method according to claim 1 wherein thiamethoxam is applied in the form of microcapsules.

4. A method of protecting wood from the attack by termites, which comprises applying to the wood to be protected or to the habitat of the termites a termiticidally effective amount of a termiticidal composition comprising:
   (a) a termiticidal active ingredient (i) consisting of thiamethoxam, in free form or in agrochemically acceptable salt form, or (ii) consisting of thiamethoxam, in free form or in agrochemically acceptable salt form and at least one insecticide mixing partner selected from fipronil and lambda-cyhalothrin; and
   (b) at least one adjuvant.

5. The method according to claim 4, characterised in that thiamethoxam in free form is used.

6. The method according to claim 4 wherein thiamethoxam is applied in the form of microcapsules.

* * * * *